United States Patent [19]

Cristalli

[11] Patent Number: 5,593,975

[45] Date of Patent: Jan. 14, 1997

[54] ADENOSINE DERIVATIVES HAVING $A_2$ AGONIST ACTIVITY

[75] Inventor: Gloria Cristalli, Camerino, Italy

[73] Assignee: Schering Corporation, Kenilworth, N.J.

[21] Appl. No.: 325,201

[22] PCT Filed: Apr. 21, 1993

[86] PCT No.: PCT/EP93/00972

§ 371 Date: Jan. 30, 1995

§ 102(e) Date: Jan. 30, 1995

[87] PCT Pub. No.: WO93/22328

PCT Pub. Date: Nov. 11, 1993

[30] Foreign Application Priority Data

Apr. 24, 1992 [IT] Italy .................................. MI92A0973

[51] Int. Cl.[6] ........................ A61K 31/70; C07H 19/167
[52] U.S. Cl. ........................................ 514/46; 536/27.22
[58] Field of Search ........................... 514/46; 536/27.22

[56] References Cited

FOREIGN PATENT DOCUMENTS

| 219876 | 4/1987 | European Pat. Off. . |
| 267878 | 5/1988 | European Pat. Off. . |
| 277917 | 8/1988 | European Pat. Off. . |
| 390112 | 3/1989 | European Pat. Off. . |
| 323807 | 7/1989 | European Pat. Off. . |
| 2203149 | 10/1988 | United Kingdom . |

OTHER PUBLICATIONS

Stone T. W., "Purine receptors and their phamacological roles," *Advances in Drug Research*, 18, (Academic Press Limited, 1989), 291–429.
Belardinelli et al, *Progress Cardiovasc. Dis.*, 1989, 32, 73–97.
Daly, J., *J. Med. Chem.*, 1982, 25 (3), 197–207.
Olsson, et al, *Physiol. Rev.*, 1990, 70 (3), 761–845.
Jacobson, et al, *J. Med. Chem.*, 1992, 3 (3), 407–422.
Bruns, et al, *Mol. Pharmacol.*, 1986, 29, 331–346.
Jarvis, et al, *J. Pharmacol Exp. Ther.*, 1989, 25 (3), 888–893.
Nair, et al, *Synthesis*, 1982, 670–672.
Bruns, et al, *Proc. Natl. Acad. Sci. USA*, 1980, 77, 5547–5551.
Conti, et al, *Eur. J. Pharmacol.*, 1990, 176, 207–212.
Collis, M., *Br. J. Pharmacol.*, 1983, 78, 207–212.
Born, et al, *J. Physiol.*, 1963, 168, 178–195.
Monopoli, et al, *Arch. Int. Pharmacodyn.*, 1987, 286, 546–254.
Cristalli, et al, *J. Med. Chem.*, 1992, 35, 2363–2368.
Matsuda, et al, *J. Med. Chem.*, 1992, 35, 241–252.
Matsuda, et al, *Chem. Pharm. Bull.*, 1985, 33 (4), 1766–1769.
Abiru, et al, *Eur. J. Pharmacol.*, 1991, 196, 69–76.
Homma et al., "Nucleosides and Nucleotides. 112. 2-(1-Hexyn-1-yl)adenosine-5'-uronamides: A New Entry of Selective $A_2$ Adenosine Receptor Agonists with Potent Antihypertensive Activity," *J. Medicinal Chem.*, 35(15), 2881–2890 (1992).

Conti et al., "Effects of Selective $A_1$ and $A_2$ Adenosine Receptor Agonists on Cardiovascular Tissues," *Naunyn-Schmiedeberg's Arch. Pharmacol.*, 348(1), 108–112 (1993).

*Primary Examiner*—John Kight
*Assistant Examiner*—L. Eric Crane
*Attorney, Agent, or Firm*—Anita W. Magatti; Eric S. Dicker

[57] ABSTRACT

Adenosine $A_2$ agonists of the formula

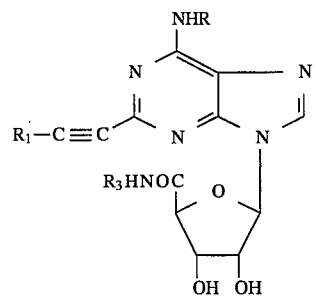

wherein

R is hydrogen, alkyl, cycloalkyl or phenylalkyl;

$R_1$ is selected from the group consisting of
 a) optionally substituted phenyl or naphthyl;
 b) —$(CH_2)_m$—Het wherein m is 0–3 and Het is a 5 or 6 membered heterocyclic aromatic or non-aromatic ring, optionally benzocondensed;
 c) cycloalkyl optionally containing unsaturations or alkenyl; and d)

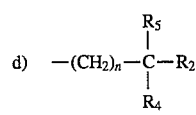

wherein n is 0–4;
 $R_2$ is hydrogen, methyl or phenyl;
 $R_5$ is hydrogen, alkyl, cycloalkyl, cycloalkenyl or phenylalkyl; or $R_2$ and $R_5$ form a 5 or 6-membered carbocyclic ring; or $R_5$ is hydrogen and $R_2$ and $R_4$ form an oxo group or a corresponding acetalic derivative;
 $R_4$ is OH, $NH_2$, dialkylamino, halogen or cyano; and $R_3$ is alkyl, cycloalkyl, phenyl or benzyl; provided that when R is different from hydrogen or when R is hydrogen and $R_3$ is phenyl or benzyl, $R_1$ can also be alkyl, useful in the treatment of cardiovascular pathologies and nervous system diseases, a process for the preparation thereof and pharmaceutical compositions containing them are disclosed.

8 Claims, No Drawings

ADENOSINE DERIVATIVES HAVING $A_2$ AGONIST ACTIVITY

The present application is the United States national application corresponding to International Application No. PCT. EP93/00972, filed Apr. 21, 1993 and designating the United States.

The present invention relates to adenosine derivatives having $A_2$ agonist activity and the use thereof in therapy.

Adenosine is known to modulate a number of physiological functions. At the cardiovascular system level, adenosine is a strong vasodilator and a cardiac depressor. On central nervous system, adenosine induces sedative, anxiolytic and antiepileptic effects. At the kidney level, it exerts a diphasic action, inducing vasoconstriction at low concentrations and vasodilatation at high doses. Adenosine acts as a lipolysis inhibitor on fat cells and as an antiaggregant on platelets (Stone T. W., Purine receptors and their pharmacological roles. In: Advances in drug research. Academic Press Limited, 1989, 18, 291–429; Progress Cardiovasc. Dis. 1989, 32, 73–97).

A number of studies showed adenosine actions are mediated by two subtypes of receptors which are located on the cell membrane: an high-affinity one, inhibiting the activity of the enzyme adenylate cyclase ($A_1$ receptor), and a low-affinity one, stimulating the activity of the same enzyme ($A_2$ receptor). (J. Med. Chem. 1982, 25, 197–207. Physiol. Rev. 1990, 70(3), 761–845. J. Med. Chem. 1992, 35, 407–422). Both receptors are widely spread in the different systems of the organism. In some tissues, however, only one of said receptors is mainly pre sent. For example, $A_1$ receptor is prevailing at the cardiac level, whereas the $A_2$ receptor is present mainly at the vascular level and on platelets.

Therefore, it is clear that compounds capable of interacting selectively with the $A_2$ receptor could have an interesting pharmacological pattern. In fact, the vasodilating activity, together with the antiaggregating action, can lead to useful therapeutical applications in the treatment of severe cardiovascular pathologies, such as ischemic cardiopathy, hypertension and atherosclerosis.

Moreover, due to the actions on central nervous system, the use of $A_2$ selective medicaments can be envisaged in the treatment of cerebrovascular ischemia, epilepsy and various emotional disorders, such as anxiety and psychosis.

The prototypical compound having activity on the $A_2$ receptor is adenosine-5'-N-ethyluronamide or NECA (Mol. Pharmacol., 1986, 25, 331–336). On the other hand, NECA is also active on the $A_1$ receptor and therefore it lacks selectivity for the adenosine receptors. Being the only available compound having $A_2$ affinity, NECA was used for pharmacological tests for the receptor binding. Only recently, the use of NECA as a prototypical $A_2$ agonist has been gradually quit since compounds were found having a certain $A_2$ receptor selectivity. Said compounds are NECA derivatives which are substituted at the C2-position with phenylamino groups. For example, compound 2-(p-(carboxyethyl)phenylethylamino)-5'-N-ethyluronamide, named CGS 21680 (J. Pharmacol Exp. Ther., 1989, 251, 888–893) has become the reference compound for the pharmacological studies on $A_2$ receptor.

Purine derivatives having a selective $A_2$ agonist activity are disclosed, for example, in GB-A-2203149, EP-A-0309112, EP-A-0267878, EP-A-0277917, EP-A-0323807.

Particularly, substitution at the 2-position of the purine group has been considered promising to give the desired selectivity (J. Med. Chem. 1992, 35, 407–422).

2-Alkynylpurine derivatives have been disclosed in EP-A-0219876.

Now it has been found that 2-alkynyladenosine derivatives substituted at the ethyne position with aryl, heterocyclic or hydroxyalkyl groups and in which the riboside residue is substituted by the N-alkyl- (or cycloalkyl)-uronamido, have surprisingly advantageous properties compared with the known compounds.

The compounds of the invention have the following general formula:

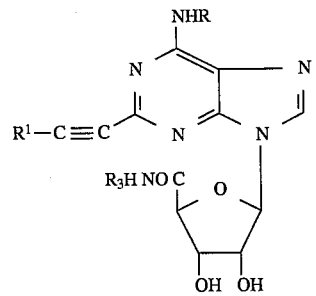

wherein

R is hydrogen, $C_1$-$C_6$ alkyl, $C_3$-$C_7$ cycloalkyl, phenyl $C_1$-$C_3$ alkyl;

$R_1$ has one of the following meanings:
a) phenyl or naphthyl optionally substituted with one to three halogen atoms (chlorine, fluorine and bromine), $C_1$-$C_6$ alkyl, $C_1$-$C_6$ haloalkyl, $C_1$-$C_6$ alkoxy, $C_1$-$C_6$ haloalkoxy, $C_2$-$C_6$ alkoxycarbonyl, $C_2$-$C_6$ alkoxyalkyl, $C_1$-$C_6$ alkylthio, thio, CHO, cyanomethyl, nitro, cyano, hydroxy, carboxy, $C_2$-$C_6$ acyl, amino, $C_1$-$C_3$ monoalkylamino, $C_2$-$C_6$ dialkylamino, methylenedioxy; aminocarbonyl;

b) a group of formula —$(CH_2)_m$—Het wherein m is 0 or an integer from 1 to 3 and Het is 5 or 6 membered heterocyclic aromatic or non aromatic ring, optionally benzocondensed, containing 1 to 3 heteroatoms selected from oxygen, nitrogen or sulphur, linked through a carbon atom or through a nitrogen atom;

c) $C_3$-$C_7$ cycloalkyl optionally containing insaturations or $C_2$-$C_4$ alkenyl;

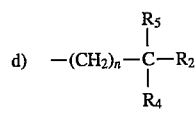

$R_2$ is hydrogen, methyl or phenyl;
$R_5$ is hydrogen, $C_1$-$C_6$ linear or branched alkyl, $C_5$-$C_6$ cycloalkyl or $C_3$-$C_7$ cycloalkenyl, phenyl-$C_1$-$C_2$-alkyl or $R_2$ and $R_5$, taken together, form a 5 or 6-membered carbocyclic ring or $R_3$ is hydrogen and $R_2$ and $R_4$, taken together, form an oxo group or a corresponding acetalic derivative;
when R is different from hydrogen and/or $R_3$ is different from ethyl, $R_1$ can also be $C_1$-$C_6$ linear or branched alkyl;
$R_4$ is OH, $NH_2$, dialkylamino, halogen, cyano;
n is 0 or 1 to 4;

Within the scope of the definitions given for formula I, the following meanings are preferred:
—for $C_1$-$C_6$ alkyl: methyl or ethyl;
—for $C_3$-$C_7$ cycloalkyl: cyclopropyl, cyclopentyl, cyclohexyl or cyclohexenyl;
—for phenyl-$C_1$-$C_2$ alkyl: benzyl or phenylethyl;
—for $C_1$-$C_6$ haloalkyl: trifluoromethyl;
—for halogen: chlorine;
—for $C_1$-$C_6$ alkoxy: methoxy or ethoxy;
—for $C_1$-$C_6$ haloalkoxy: trifluoromethoxy or difluoromethoxy;
—for $C_2$-$C_6$ alkoxycarbonyl: methoxycarbonyl or ethoxycarbonyl;

—for $C_2$-$C_6$ alkoxyalkyl: methoxymethyl, methoxyethyl or ethoxymethyl;
—for $C_1$-$C_6$ alkylthio: methylthio;
—for $C_2$-$C_6$ acyl: acetyl;
—for $C_1$-$C_3$ monoalkylamino: methylamino, ethylamino, isopropylamino;
—for $C_2$-$C_6$ dialkylamino: dimethylamino, diethylamino, methylethylamino, methylisopropylamino, diisopropylamino;
—for heterocyclic aromatic or non aromatic ring containing 1 to 3 N, S, O atoms: pyridyl, thienyl, furyl, imidazolyl, thiazolyl, pyrazolyl, triazolyl.
—for acetalic derivative: diethylacetal.

Preferred compounds of formula I are:
1. Compounds in which R is hydrogen;
2. Compounds in which R is $C_3$-$C_7$ cycloalkyl; (R) or (S)-phenylisopropyl;
3. Compounds in which $R_1$ is phenyl or naphthyl optionally monosubstituted with one of the substituents in point a);
4. Compounds in which $R_1$ is phenyl optionally substituted with one of the substituents in point a);
5. Compounds in which $R_1$ is phenyl, 2-, 3- or 4-nitrophenyl, 2-, 3- or 4-aminophenyl, 2-, 3- or 4-methylphenyl, 2-, 3- or 4-acetylphenyl, 4-cyanomethylphenyl, 4-formylphenyl, 2-, 3- or 4-trifluoromethylphenyl, 2-, 3- or 4-fluorophenyl, 2-, 3- or 4-methoxyphenyl, 2-, 3- or 4-carbomethoxyphenyl, 2-, 3- or 4-carbethoxyphenyl;
6. Compounds in which $R_1$ is cyclohexyl or 1-cyclohexenyl;
7. Compounds in which $R_1$ is 2-thienyl, 2-pyridyl, 4-pyridyl, 4-pyrazolyl, 2-furyl, 3-furyl, 2-thiazolyl, 1-imidazolylmethyl, 1-triazolylmethyl.
8. Compounds in which $R_1$ is

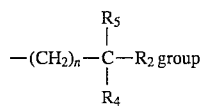

wherein $R_2$ is hydrogen or methyl, $R_5$ is hydrogen or $C_1$-$C_6$ alkyl, $R_4$ is hydroxy or amino.
9. Compounds in which R is hydrogen and $R_1$ has the meanings according to points 2–7 above.

The claimed compounds can be used as anhydrous bases, solvates or pharmaceutically acceptable acid salts.

Compounds I can be prepared according to the following general schemes:

Scheme I

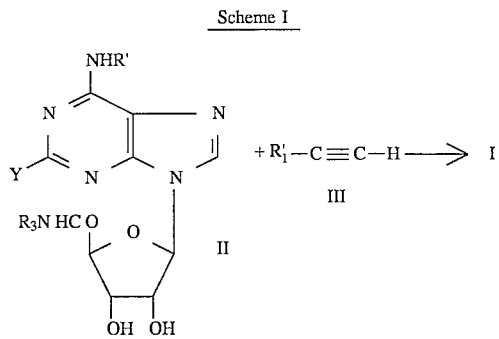

Scheme II

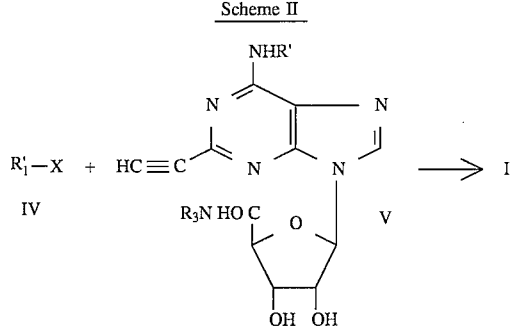

In schemes I and II, R' and $R'_1$ have the same meanings as R and $R_1$ or they are groups which can be converted into R and $R_1$, respectively, for example by removing any protecting groups which can be present in R' and $R'_1$ compatible with the reaction conditions; Y is Br or I and X is chlorine, bromine or iodine.

Preferably Y is iodine and X is bromine or iodine.

The reactions reported in schemes I and II are carried out in the presence of catalysts (for example: bis(triphenylphosphine) palladium dichloride and a cuprous halide) and of a suitable acid-binding agent, such as an organic base (for example: triethylamine, diisopropylethylamine or pyridine).

As the solvent, a substituted amide (such as dimethylformamide), an ether (such as dioxane or tetrahydrofuran), acetonitrile or optionally a mixture of two or more of said solvents, are preferably used.

The compounds of formula II, in which Y is iodine and R' is hydrogen, can be prepared from 2-iodoadenosine (Synthesis, 1982, 670–672) according to the following scheme III Scheme III

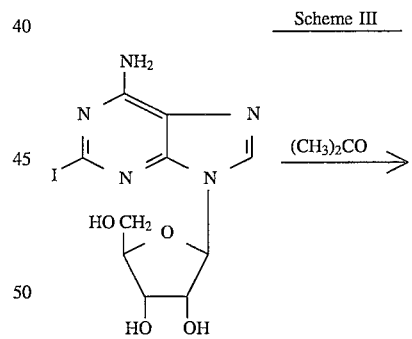

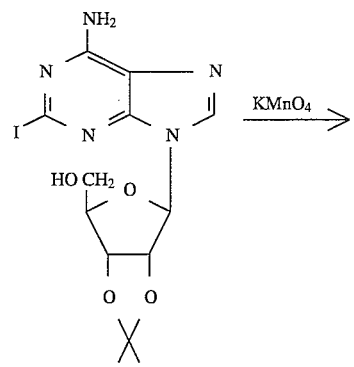

-continued
Scheme III

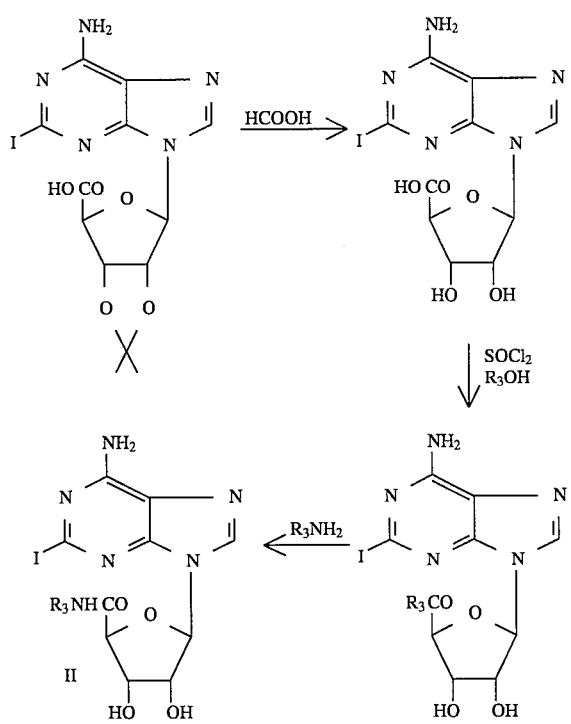

The compounds of formula can be prepared in which Y is iodine and R' is different from hydrogen can be prepared according to the following Scheme IV In the above scheme IV, R, $R_1$ and $R_3$ are as above defined.

The compounds of formula VI are novel and they are a further object of the invention, as intermediates.

The compounds of formula V are prepared by reaction of compounds II with an acetylene derivative, for example 1-trimethylsilylethynyle, under the conditions reported for the reaction between compounds II and III. Compounds V are novel and they are a further object of the invention, as intermediates.

Compounds III and IV are known or they can be prepared according to well-known methods.

Compounds I have a strong $A_2$ agonist selectivity and therefore they are useful for the treatment of cardiovascular pathologies such as cardiac ischemia, hypertension and atherosclerosis and of diseases of central nervous system such as cerebrovascular ischemia, epilepsy and emotional disorders (anxiety and psychosis).

Pharmacological Activity

The pharmacological properties of the disclosed compounds can be shown in the most suitable experimental models both in vitro and in vivo.

Adenosine $A_2$ receptor affinity was tested by means of receptor binding techniques on rat (Wistar strain) brain striatum, which is a tissue rich in $A_2$ receptors. Compound 3H-CGS 21680 (J. Pharm. Exp. Ther. 1989, 251, 888–893) was used as the radioligand.

The $A_1$ receptor affinity was tested with receptor binding techniques on rat (Wistar strain) cerebellar cortex membranes, which are tissues rich in $A_1$ receptors. $^3$H-Cyclohexyl-adenosine, $^3$H-CHA (Proc. Natl. Acad. Sci.—USA—1980, 77, 5547–5551) was used as the radioligand. The Scheme IV

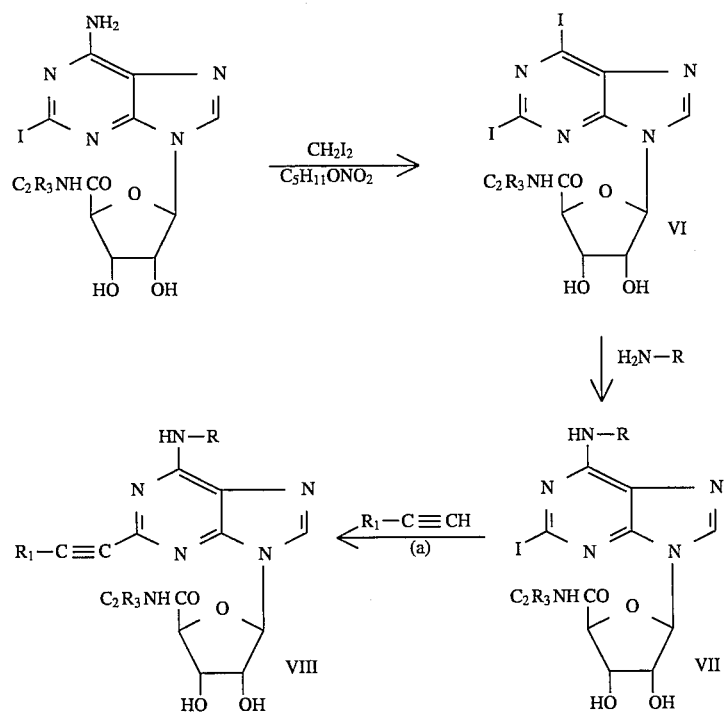

(a) = $(Ph_3P)PdCl_2$; CuI; $Et_3N$ affinity for the $A_1$ or $A_2$ receptor shown by each compound was compared to evaluate selectivity for the $A_2$ receptor. A number of experimental proofs evidence a marked relationship between the affinity found with binding techniques in brain tissues and the physiological effects modulated by adenosine receptors.

In order to evaluate the functional response of specific tissues to the disclosed compounds, the isolated organs models were used. Particularly, the vasodilatation response, which is modulated by $A_2$ receptors, was studied to the tested compounds (Eur. J. Pharmacol 1990, 176, 207–212) on rat aorta in which a contraction had been induced by a prostaglandin compound ($PGF_2\infty$). Any chronotropic negative effects of the various compounds (Br. J. Pharmacol 1983, 78, 207–212) were tested on rat isolated heart atria, whose rate is known to be modulated by $A_1$ receptors. From the comparison of the activities shown by each compound for the functional responses of the $A_2$ type (vasodilatation) or the $A_1$ type (reduction in the heart rate), the potential anti-ischemic and antihypertensive activities of the tested compounds can be evaluated, as well as the absence of undesired effects on the heart rate.

In order to evaluate the potential anti-atherosclerosis and anti-ischemic activities, the inhibiting effect of various compounds on platelet aggregation induced by aggregation agents such as adenosine diphosphate (ADP) (J. Physiol. 1963, 168, 178–195) was studied. The test is particularly important as only the $A_2$ receptor is present on the platelet cell membrane.

The in vivo activity was evaluated in Swiss mice and spontaneously hypertensive rats (SHR). The behaviour response to a treatment with various doses of the tested compounds administered parenterally was evaluated. To test the antiepileptic action, the property of the novel compounds to antagonize the convulsions induced by pentylenetetrazole was evaluated in the mouse.

The antihypertensive activity was tested measuring the systolic arterial pressure by means of the "tail-cuff." technique (Arch. Int. Pharmacodyn., 1987, 286, 546–254) in SHR rats conditioned to the experimental environment.

The tested compounds were administered parenterally at increasing doses and arterial pressure and heart rate were measured at various times from the treatment.

The compounds of formula I showed a marked $A_2$ affinity with Ki ranging from 7 to 200 nM. The $A_2$ selectivity for some compounds is higher than 100 and anyhow it turned out to be markedly higher than that of the prototypical compound NECA. In the platelet aggregation test, said compounds proved to be effective anti-platelet aggregation agents, with $IC_{50}$s of 0,1–10 μM. The vasodilatation activity is clear, as evidenced by $ED_{50}$s of 0,1–10 μM, whereas the same concentrations did not change the heart rate of isolated atria. In the in vivo models, the tested compounds showed a depressing activity on central nervous system, they antagonized the convulsions induced by pentylenetetrazole and reduced the arterial pressure without changing significantly the heart rate. The compounds turned out to be active at doses from 0.001 to 3 mg/kg intraperitoneally.

For the envisaged therapeutical uses, compounds I will be formulated as suitable pharmaceutical compositions, which can be administered, for example, by the oral or parenteral routes, using known techniques and excipients, as de scribed for example in Remington's Pharmaceutical Sciences Handbook, Mack Pub. Co., NY, USA, XVII ed. The daily dosage will depend, of course, on many factors (severity of the pathology to treat, patient conditions, toxicology and pharmacokinetic of the selected compound) but generally it will range from 0,01 to 10 mg/kg of body weight, preferably from 0,1 to 1 mg/kg, optionally subdivided in more administrations. Examples of pharmaceutical compositions comprise capsules, tablets, solutions, syrups, vials, controlled-release forms and the like.

The following examples illustrate the invention.

EXAMPLE 1

N-ethyl-1'-deoxy-1'-(6-amino-2-iodo-9H-purin-9-yl)-β-D-ribofuranuronamide a) A solution of 2 g (5.08 mmoles) of 2-iodoadenosine in 100 ml of acetone was added with 9.6 g of p-toluenesulfonic acid. The reaction mixture was stirred at room temperature for 1 h, then, after addition of 15 g of $NaHCO_3$, it was stirred again for 3 h. The solid was removed and washed 2 times with ethyl acetate and the filtrate was concentrated to dryness. The residue was flash chromatographed on a silica gel column eluting with $CHCl_3$-MeOH (99:1) to give 1.62 g (74%) of 6-amino-2-iodo-9-(2', 3'-O-isopropylidene-β-D-ribofuranosyl)-9-H-purine as a solid:

m.p. 185°–187° C.;

$^1$H NMR ($Me_2SO$-$d_6$) δ1.33 and 1.54 (s, 3H each, C($\underline{CH}_3$)$_2$, 3.53 (m, 2H, $CH_2$-5'), 4.19 (m, 1H, H-4'), 5.07 (t, 1H, OH), 4.93 (m, 1H, H-3'), 5.27 (m, 1H, H-2'), 6.05 (d, J=2.5 Hz, 1H, H-1'), 7.76 (s, 2H, $NH_2$), 8.28 (s, 1H, H-8). Anal. ($C_{13}H_{16}IN_5O_4$) C, H, N.

b) A stirred solution of 1.6 g (3.7 mmoles) of the product obtained in a) in 200 ml of $H_2O$ was added with 0.60 g of KOH and, dropwise, with a solution of 1.70 g (10.8 mmoles) of $KMnO_4$ in 50 ml of $H_2O$. The mixture was left aside in the dark at room temperature for 20 h. The reaction mixture was cooled to 5°–10° C. and then decolorized with a solution of 4 ml of 30% $H_2O_2$ in 16 ml of water, keeping the temperature under 10° C. with an ice-salt bath. The mixture was filtered through Celite and the filtrate was concentrated under vacuum to about 15 ml and then acidified to pH 4 con 2N HCl. The resulting precipitate was filtered, and subsequently washed with water, acetone and ether to give 1.25 g (76%) of 1'-deoxy-1'-(6-amino-2-iodo-9$\underline{H}$-purin-9-yl)-2', 3'-O-isopropylidene-β-$\underline{D}$-ribofuranuronic acid as a white solid:

m.p. 187°–190° C.;

IR vmax 1590, 1640 cm$^{-1}$ (COOH); $^1$H NMR ($Me_2SO$-$d_6$) δ1.33 and 1.49 (s, 3H each, C($\underline{CH}_3$)$_2$, 4.64 (s, 1H, H-4'), 5.35 (d, $J_{3',2'}$=5.6 Hz, 1H, H-3'), 5.41 (d, $J_{2',3'}$=5.6 Hz, 1H, H-2'), 6.23 (s, 1H, H-1'), 7.53 (s, 1H, COOH), 7.67 (s, 2H, $NH_2$), 8.17 (s, 1H, H-8). Anal. ($C_{13}H_{14}IN_5O_5$) C, H, N.

c) A solution of 1.72 g (3.85 mmoles) of the product obtained in b) in 80 ml of 50% formic acid was stirred at 80° C. for 1.5 h. The reaction mixture was evaporated under vacuum and the residue was dissolved in water, and the solution was evaporated. This process was repeated several times, until there was no more odor of formic acid in the residue. Recrystallization from water yielded 1.33 g (85%) of 1'-deoxy-1'-(6-amino-2-iodo-9$\underline{H}$-purin-9-yl)-β-$\underline{D}$-ribofuranuronic acid as a white solid:

m.p. 217°–220° C. (dec.)

$^1$H NMR ($Me_2SO$-$d_6$) δ4.28 (m, 1H, H-3'), 4.41 (d, J=2.1 Hz, 1H, H-4'), 4.81 (m, 1H, H-2'), 5.95 (d, J=6.7 Hz, 1H, H-1'), 7.78 (s, 2H, $NH_2$), 8.38 (s, 1H, H-8), 12.98 (br s, 1H, COOH). Anal. ($C_{10}H_{10}IN_5O_5$) C, H, N.

d) A cooled (5° C.) and stirred solution of 1.29 g (3.17 mmoles) of the product obtained in c) in 150 ml of absolute ethanol was added dropwise with 1.15 ml of ice-cooled SOCl$_2$. The mixture was stirred at room temperature overnight and then brought to pH 8 with saturated aqueous sodium bicarbonate. The mixture was filtered and the filtrate was concentrated under vacuum. The recrystallization of the residue from water-ethanol (1:1) gave 900 mg (65%) of ethyl 1'-deoxy-1'-(6-amino-2-iodo-9H-purin-9-yl)-β-D-ribofuranuronate as a white solid:

m.p. 221°–223° C. (dec.)

IR νmax 1728 cm$^{-1}$ (COOEt); $^1$H NMR (Me$_2$SO-D$_6$) δ1.21 (t, 3H, —CH$_2$CH$_3$), 4.18 (q, 2H, —CH$_2$CH$_3$), 4.34 (m, 1H, H-3'), 4.47 (s, 1H, H-4'), 4.58 (m, 1H, H-2'), 5.96 (d, J=6.7 Hz, 1H, H-1'), 7.74 (s, 2H, NH$_2$), 8.33 (s, 1H, H-8). Anal. (C$_{12}$H$_{14}$IN$_5$O$_5$) C, H, N.

e) A mixture of 620 mg of the product obtained in the step d) and 18 ml of dry ethylamine was stirred at −20° C. for 3 h and then at room temperature overnight. The reaction mixture was diluted with absolute ethanol and the precipitated product was filtered and washed with dry ether to give 530 mg (85%) of N-ethyl-1'-deoxy-1'-(6-amino-2-iodo-9H-purin-9-yl)-β-D-ribofuranuronamide as a pure solid:

m.p. 232°–234° C.

IR νmax 1637, 1560 cm$^{-1}$ (C=O, amide); $^1$H NMR (Me$_2$SO-d$_6$) δ1.06 (t, 3H, —CH$_2$CH$_3$), 3.28 (m, 2H, —CH$_2$CH$_3$), 4.16 (m, 1H, H-3'), 4.31 (d, J=2,1 Hz, 1H, H-4'), 4.58 (m, 1H, H-2'), 5.91 (d, 1H, J=7.3 Hz, H-1'), 7.79 (s, 2H, NH$_2$), 8.15 (t, 1H, NH), 8.40 (s, 1H, H-8). Anal. (C$_{12}$H$_{15}$IN$_6$O$_4$) C, H, N.

EXAMPLE 2

A solution of 250 mg (0.58 mmole) of the product of Example 1 in 10 ml of dry acetonitrile, 5 ml of DMF and 2.5 ml of triethylamine under nitrogen was added with 8.1 mg (0.0115 mmole) of bis(triphenylphosphine)palladium dichloride and 0.58 mg (0.003 mmole) of cuprous iodide. The mixture was added with 2.9 mmoles of phenylacetylene and the reaction mixture was stirred under nitrogen atmosphere at room temperature for 2 h. The solvent was evaporated off under vacuum and the residue was chromatographed on a silica gel column, eluting with a chloroform-benzene-methanol 78:10:12 mixture, to give N-ethyl-1'-deoxy-1'-(6-amino-2-phenylethynyl-9H-purin-9-yl)-β-D-ribofuranuronamide (yield: 60%):

m.p. 175°–178° C. (dec)

$^1$H NMR (Me$_2$SO-d$_6$) δ1.02 (t, 3H, —CH$_2$CH$_3$), 3.28 (m, 2H, —CH$_2$CH$_3$), 4.15 (m, 1H, H-3'), 4.31 (d, J=1.2 Hz, 1H, H-4'), 4.62 (m, 1H, H-2'), 5.97 (d, 1H, J=7.5 Hz, H-1'), 7.58 (d, J=7.8 Hz, 2H, H-Ph), 7.46 (m, 2H, H-Ph), 7.66 (s, 2H, NH$_2$), 8.49 (s, 1H, H-8), 8.60 (t, 1H, NH). Anal. (C$_{20}$H$_{20}$N$_6$O$_4$.H$_2$O) C, H, N.

EXAMPLES 3–35

By the same method of Example 2, the following compounds I, wherein R$_3$ is ethyl and R is hydrogen, were prepared.

| Ex. | R$_1$ | m.p. (°C.) | Yield (%) | Reaction time (h) |
|---|---|---|---|---|
| 3 | 4-NO$_2$—Ph | 180–183 (dec) | 80 | 4 |
| 4 | 4-NH$_2$—Ph | 225–228 (dec) | 60 | 4 |
| 5 | 4-NH$_2$—CO—Ph | 240–243 (dec) | 55 | 16 |
| 6 | 4-CH$_3$—Ph | 210–213 (dec) | 50 | 3 |
| 7 | 4-CHO—Ph | 210–213 (dec) | 80 | 6 |
| 8 | 4-CH$_3$—CO—Ph | 185–188 (dec) | 60 | 20 |
| 9 | 4-CNCH$_2$—Ph | 230–232 (dec) | 55 | 20 |
| 10 | naphthyl | 225–228 (dec) | 45 | 20 |
| 11 | —C(CH$_3$)(OH)—Ph | 203–205 (dec) | 75 | 20 |
| 12 | HO(CH$_2$)$_4$ | 245–247 | 69 | 24 |
| 13 | cyclohexyl | 200–203 (dec) | 68 | 6 |
| 14 | cyclohexenyl | 210–213 (dec) | 75 | 3 |
| 15 | (CH$_3$)$_3$Si | 208–211 (dec) | 95 | 16 |
| 16 | (CH$_2$)$_3$Cl | 156–158 | 52 | 20 |
| 17 | (CH$_2$)$_3$CN | 131–134 | 65 | 48 |
| 18 | CH$_2$OH | 173–175 (dec) | 52 | 3 |
| 19 | —CH(OH)—Ph | 150–152 (dec) | 67 | 20 |
| 20 | CH$_2$CH$_2$OH | 245–248 (dec) | 70 | 20 |
| 21 | —CH(OH)—CH$_3$ | 211–214 (dec) | 52 | 20 |
| 22 | (CH$_2$)$_3$OH | 230–232 | 57 | 20 |
| 23 | CH$_2$—CH(OH)—CH$_3$ | 232–234 (dec) | 39 | 5 |
| 24 | —CH(OH)—CH$_2$—CH$_3$ | 148–150 (dec) | 37 | 5 |
| 25 | —CH(CH$_3$)—CH$_2$—CH(OH)—CH$_3$ | 135–137 | 41 | 5 |
| 26 | 1-hydroxycyclopentyl | 153–155 | 30 | 20 |

| Ex. | R₁ | m.p. (°C.) | Yield (%) | Reaction time (h) |
|---|---|---|---|---|
| 27 | NH₂–cyclohexyl  | 211–213 | 76 | 30 |
| 28 | CH₂NH₂ | — | 52 | 36 |
| 29 | CH₂CH₂N(CH₃)₂ 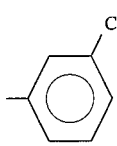 | 227–230 (dec) | 61 | 20 |
| 30 | —C(CH₃)=CH₂ | 175–177 (dec) | 65 | 20 |
| 31 | –phenyl–CHO 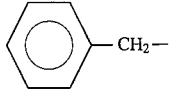 | 164–165 (dec) | 50 | 36 |
| 32 | —CH(OC₂H₅)₂ | 184–187 | 56 | 48 |
| 33 | –CH₂–phenyl 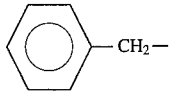 | 124–126 | 53 | 4 |
| 34 | –CH₂–CH₂–phenyl 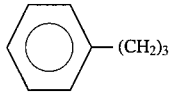 | 143–145 | 53 | 16 |
| 35 | –(CH₂)₃–phenyl 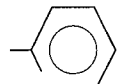 | 128–130 | 53 | 16 |

Anal. (CHN) and ¹H-NMR in agreement with the given formulas.

EXAMPLE 36 a) N-ethyl-1'-deoxy-1'-[6-amino-2-ethynyl-9H-purin-9-yl]-β-D-ribofuranuronamide 1.6 mg (3.96 mmoles) of the product obtained in Example 15 in 30 ml of methanol were added with 0.32 g of KOH in 10 ml of methanol. The reaction mixture was stirred at room temperature for 1 h and then the solvent was removed under vacuum. The residue was partitioned between ethyl acetate and water and the combined organic layers were dried (Na₂SO₄) and evaporated to give 1.0 g (81%) of the title compound as a chromatographically pure solid:

m.p.: 245°–248° C. (dec)

¹H NMR (Me₂SO-d₆) δ1.04 (t, 3H, —CH₂$\underline{CH_3}$), 3.26 (m, 2H, —$\underline{CH_2}$CH₃), 4.10 (s, 1H, —C≡CH), 4.12 (m, 1H, H-3'), 4.29 (d, J=1.5, 1H, H-4'), 4.55 (m, 1H, H-2'), 5.92 (d, 1H, J=7.5 Hz, H-1'), 7.62 (s, 2H, NH₂), 8.46 (s, 1H, H-8), 8.63 (t, 1H, NH). Anal. (C₁₄H₁₆N₆O₄·H₂O) C, H, N.

b) N-ethyl-1'-deoxy-1'-{6-amino-2-(4-trifluoromethyl)phenyl]ethynyl-9h-purin-9-yl}-β-D-ribofuranuronamide A solution of 200 mg (0.66 mmole) of the compound of step a) in 10 ml of dry acetonitrile, 5 ml of DMF and 2.6 ml of triethylamine under nitrogen atmosphere, was added with 9.24 mg (0.013 mmole) of bis(triphenylphosphine)palladium dichloride and 0.66 mg (0.0035 mmole) of cuprous iodide. The mixture was added with 3.3 mmoles of 4-trifluoromethyl-iodobenzene and the reaction mixture was stirred under nitrogen atmosphere for 1 h at 50 ° C. The solvent was evaporated under vacuum and the residue was chromatographed on a silica gel column, eluting with chloroform-benzene-methanol (80:10:10). The title product was obtained in a 65% yield.

m.p.: 224°–227° C. (dec)

¹H NMR (Me₂SO-d₆) δ1.01 (t, 3H, —CH₂$\underline{CH_3}$), 3.26 (m, 2H, —$\underline{CH_2}$CH₃), 4.14 (m, 1H, H-3'), 4.31 (s, 1H, H-4'), 4.61 (m, 1H, H-2'), 5.97 (d, 1H, J=7.5 Hz, H-1'), 7.71 (s, 2H, NH₂), 7.81 (s, 4H, H-Ph), 8.52 (s, 1H, H-8), 8.58 (t, 1H, NH). Anal. (C₂₁H₁₉F₃N₆O₄·H₂O) C, H, N.

EXAMPLES 37–43

By the same method of Example 3 6, the following compounds I, wherein R is hydrogen and R₃ is ethyl, were prepared.

| Ex. | R₁ | m.p. (°C.) | Yield (%) | Reaction time (h) |
|---|---|---|---|---|
| 37 | pyridyl 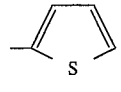 | 213–215 (dec) | 88 | 20 |
| 38 | thienyl 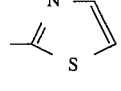 | 245–248 (dec) | 82 | 16 |
| 39 | thiazolyl 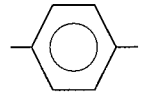 | 210–213 (dec) | 67 | 5 |
| 40 | –phenyl–OH  | 200–202 | 63 | 16 |
| 41 | –phenyl–F  | 184–185 (dec) | 55 | 16 |
| 42 | –phenyl–OCH₃ 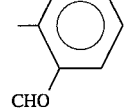 | 151–154 (dec) | 49 | 3 |
| 43 | –phenyl–CHO | 189–191 | 23 | 5 |

EXAMPLES 44–46

By reacting the compound of Example 1d with an amine selected from:

—cyclopentylamine;
—benzylamine;
—aniline;
at room temperature for 20 hours, the following compounds as chromatographically pure oils were obtained after the usual work-up (solution concentrated to dryness and the residue chromatographed on a silica gel column eluting with a suitable mixture of solvents):

N-cyclopentyl-1'-deoxy-1'-(6-amino-2-iodo-9H-purin-9-yl)-β-D-ribofuranuronamide (IIa)

$^1$H NMR (Me$_2$SO-d$_6$) δ1.33–1.98 (m, 8H, H-cyclopentyl), 4.06 (m, 1H, H-cyclopentyl), 4.19 (m, 1H, H-3'), 4.35 (d, 1H, J=2.4 Hz, H-4'), 4.58 (m, 1H, H-2'), 5.93 (d, 1H, J=6.4 Hz, H-1'), 7.77 (s, 2H, NH$_2$), 8.08 (d, 1H, J=7.5 Hz, NH), 8.50 (s, 1H, H-8). Anal. (C$_{15}$H$_{19}$IH$_6$O$_4$) C, H, N.

N-benzyl-1'-deoxy-1'-(6-amino-2-iodo-9H-purin-9-yl)-β-D-ribofuranuronamide (IIb)

$^1$H NMR (Me$_2$SO-d$_6$) δ4.22 (m, 1H, H-3'), 4.42 (d, 1H, J=1.5 Hz, H-4'), 4.46 (m, 2H, CH$_2$), 4.59 (m, 1H, H-2'), 5.94 (d, 1H, J=7.2 Hz, H-1'), 7.28 (m, 5H, H-Ph), 7.81 (s, 2H, NH$_2$), 8.40 (s, 1H, H-8), 8.74 (t, 1H, HN). Anal. (C$_{17}$H$_{17}$IN$_6$O$_4$) C, H, N.

N-phenyl-1'-deoxy-1'-(6-amino-2-iodo-9H-purin-9-yl)-β-D-ribofuranuronamide (IIc)

$^1$H NMR (Me$_2$SO-d$_6$) δ4.35 (m, 1H, H-3'), 4.58 (d, J=1.5 Hz, 1H, H-4'), 4.66 (m, 1H, H-2'), 6.01 (d, 1H, J=6.6 Hz, H-1'), 7.11 (t, 1H, H-Ph), 7.34 (t, 2H, H-Ph), 7.65 (d, 2H, H-Ph), 7.78 (s, 2H, NH$_2$), 8.52 (s, 1H, H-8), 10.16 (s, 1H, NH). Anal. (C$_{16}$H$_{15}$IN$_6$O$_4$) C, H, N.

Said compounds were reacted with 1-hexyne according to the procedure of Example 2 to give the compounds of formula I reported in the following Table.

the residue was chromatographed on a flash silica gel column eluting with a gradient from CHCl$_3$ to CHCl$_3$-MeOH (98:2) to give 285 mg (45%) of the title compound as a chromatographically pure oil.

$^1$H NMR (Me$_2$SO-d$_6$) δ1.04 (t, 3H, CH$_2$CH$_3$), 3.19 (m, 2H, CH$_2$CH$_3$), 4.28 (m, 1H, H-3'), 4.36 (s, 1H, H-4'), 4.70 (m, 1H, H-2'), 6.03 (d, 1H, J=6.4 Hz, H-1'), 8.15 (t, 1H, NH), 8.98 (s, 1H, H-8). Anal. (C$_{12}$H$_{13}$I$_2$N$_5$O$_4$) C, H, N.

b) N-ethyl-1'-deoxy-1'-(6-cyclopentylamino-2-iodo-9H-purin-9-yl)-β-D-ribofuranuronamide (VII)

To 240 mg (0.44 mmol) of N-ethyl-1'-deoxy-1'-(2,6-diiodo-9H-purin-9-yl)-β-D-ribofuranuronamide was added 10 ml of cyclopentylamine and the mixture was stirred at room temperature for 4 h. The solution was concentrated to dryness and the residue was chromatographed on a silica gel column eluting with CHCl$_3$-MeOH (96:4) to give 160 mg (72%) of the title compound as a chromatographically pure oil.

$^1$H NMR (Me$_2$SO-d$_6$) δ1.07 (t, 3H, CH$_2$CH$_3$), 1.48–2.08 (m, 8H, H-cyclopentyl), 3.23 (m, 2H, CH$_2$CH$_3$), 4.18 (m, 1H, H-3'), 4.32 (d, 1H, J=1.7 Hz, H-4'), 4.44 (m, 1H, H-cyclopentyl), 4.60 (m, 1H, H-2'), 5.92 (d, 1H, J=7.2 Hz, H-1'), 8.16 (t, 1H, NHCH$_2$), 8.29 (d, 1H, J=7.7 Hz, NH), 8.41 (s, 1H, H-8). Anal. (C$_{17}$H$_{23}$IN$_6$O$_4$) C, H, N.

c) N-ethyl-1'-deoxy-1'-[6-cyclopentylamino-2-(1-hexyn-1-yl)-9H-purin-9-yl]-β-D-ribofuranuronamide (VIII)

The title compound was prepared according to Example 2.

Reaction time: 16 h.

Chromatographical system: chloroform-methanol (95:5)

| Ex. | R | R$_1$ | R$_3$ | m.p. (°C.) | Yield (%) | Reaction time (h) |
|---|---|---|---|---|---|---|
| 44 | H | —(CH$_2$)$_3$—CH$_3$ | cyclopentyl | 145–147 | 48 | 40 |
| 45 | H | —(CH$_2$)$_3$—CH$_3$ | —CH$_2$—phenyl | 128–130 | 37 | 40 |
| 46 | H | —(CH$_2$)$_3$—CH$_3$ | phenyl | — | 35 | 40 |

Anal. (CHN) and 1H-NMR in agreement with the given formulas.

EXAMPLE 47 a) N-ethyl-1'-deoxy-1'-(2,6-diiodo-9H-purin-9-yl)-β-D-ribofuranuronamide (VI)

To 0.5 g (1.16 mmol) in 10 ml of DMF was added 1.7 ml of isopentyl nitrite and 5.6 ml of diiodometane and the mixture was heated at 85° C. under a N$_2$ atmosphere for 2 h. The solvent was removed under pressure (oil pump) and Yield: 57% m.p.: 120°–122° C.

$^1$H NMR (Me$_2$SO-d$_6$) δ0.92 (t, 3H, CH$_2$CH$_3$), 1.08 (t, 3H, NCH$_2$CH$_3$), 1.35–2.07 (m, 12H, H-cyclopentyl and CH$_2$CH$_2$), 2.44 (m, 2H, CH$_2$C≡C), 3.31 (m, 2H, NCH$_2$CH$_3$), 4.12 (m, 1H, H-3'), 4.31 (s, 1H, H-4'), 4.60 (m, 2H, H-2' and H-cyclopentyl), 5.94 (d, 1H, J=7.7 Hz, H-1'), 8.03 (d, 1H, NH), 8.43 (s, 1H, H-8), 8.76 (t, 1H, NHCH$_2$). Anal. (C$_{23}$H$_{32}$N$_6$O$_4$.H$_2$O) C, H, N.

I claim:
1. A compound represented by the structural formula

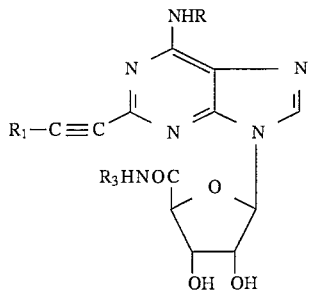

wherein
R is hydrogen, $C_1$-$C_6$ alkyl, $C_3$-$C_7$ cycloalkyl or phenyl-$C_1$-$C_3$ alkyl;
$R_1$ is selected from the group consisting of
 a) phenyl or naphthyl optionally substituted with one to three halogen atoms selected from the group consisting of chloro, fluoro and bromo, $C_1$-$C_6$ alkyl, $C_1$-$C_6$ haloalkyl, $C_1$-$C_6$ alkoxy, $C_1$-$C_6$ haloalkoxy, $C_2$-$C_6$ alkoxycarbonyl, $C_2$-$C_6$ alkoxyalkyl, $C_1$-$C_6$ alkylthio, thio, CHO, cyanomethyl, nitro, cyano, hydroxy, carboxy, $C_2$-$C_6$ acyl, amino, $C_1$-$C_3$ monoalkylamino, $C_2$-$C_6$ dialkylamino, methylenedioxy or aminocarbonyl;
 b) a group of formula —$(CH_2)_m$—Het wherein m is 0 or an integer from 1 to 3 and Het is a 5- or 6-membered heterocyclic aromatic or non-aromatic ring, optionally benzocondensed, containing 1 to 3 heteroatoms selected from the group consisting of oxygen, nitrogen and sulphur, linked through a carbon atom or through a nitrogen atom;
 c) $C_3$-$C_7$ cycloalkyl optionally containing unsaturations or $C_2$-$C_4$ alkenyl; and
 d) 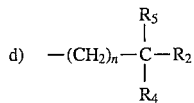

wherein
n is 0 or 1 to 4;
$R_2$ is hydrogen, methyl or phenyl;
$R_4$ is OH, $NH_2$, dialkylamino, halogen or cyano;
$R_5$ is hydrogen, $C_1$-$C_6$ linear or branched alkyl, $C_5$-$C_6$ cycloalkyl, $C_3$-$C_7$ cycloalkenyl or phenyl-$C_1$-$C_2$-alkyl; or $R_2$ and $R_5$, taken together, form a 5 or 6-membered carbocyclic ring; or $R_5$ is hydrogen and $R_2$ and $R_4$, taken together, form an oxo group or a corresponding acetalic derivative; and
$R_3$ is $C_1$-$C_6$ alkyl, $C_3$-$C_7$-cycloalkyl, phenyl or benzyl; provided that when R is different from hydrogen or when R is hydrogen and $R_3$ is cyclopentyl, phenyl or benzyl, $R_1$ can also be $C_1$-$C_6$ linear or branched alkyl.

2. Compounds according to claim 1 in which R is hydrogen or cyclopentyl.

3. Compounds according to claim 1 which $R_1$ is phenyl, 2-, 3- or 4-nitrophenyl, 2-, 3- or 4-aminophenyl, 2-, 3- or 4-methylphenyl, 2-, 3- or 4-acetyl-phenyl, 4-cyanomethylphenyl, 4-formylphenyl, 2-, 3- or 4-trifluoromethylphenyl, 2-, 3- or 4-fluorophenyl, 2-, 3- or 4-methoxyphenyl, 2-, 3- or 4-carbomethoxyphenyl, 2-, 3- or 4-carbethoxyphenyl, cyclohexyl, 1-cyclohexenyl or hydroxyphenyl.

4. Compounds according to claim 1 in which $R_1$ is 2-thienyl, 2-pyridyl, 4-pyridyl, 4-pyrazolyl, 2-furyl, 3-furyl or 2-thiazolyl.

5. Compounds according to claim 1 in which $R_1$ is a group

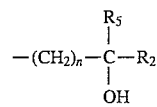

wherein $R_2$ and $R_5$ are hydrogen and n is an integer from 1 to 4, or $R_2$ is phenyl, $R_5$ is hydrogen and n is zero.

6. A compound according to claim 1 wherein $R_3$ is cyclopentyl, benzyl or phenyl.

7. A compound represented by the structural formula

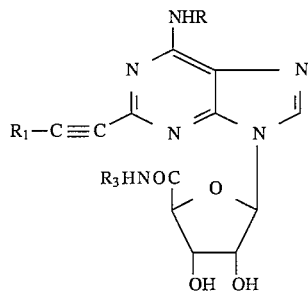

wherein
R is hydrogen, $C_1$-$C_6$ alkyl, $C_3$-$C_7$ cycloalkyl or phenyl-$C_1$-$C_3$ alkyl;
$R_1$ is selected from the group consisting of
 a) phenyl or naphthyl optionally substituted with one to three halogen atoms selected from the group consisting of chloro, fluoro and bromo, $C_1$-$C_6$ alkyl, $C_4$-$C_6$ haloalkyl, $C_1$-$C_6$ alkoxy, $C_1$-$C_6$ haloalkoxy, $C_2$-$C_6$ alkoxycarbonyl, $C_2$-$C_6$ alkoxyalkyl, $C_1$-$C_6$ alkylthio, thio, CHO, cyanomethyl, nitro, cyano, hydroxy, carboxy, $C_2$-$C_6$ acyl, amino, $C_1$-$C_3$ monoalkylamino, $C_2$-$C_6$ dialkylamino, methylenedioxy or aminocarbonyl;
 b) a group of formula —$(CH_2)_m$—Het wherein m is 0 or an integer from 1 to 3 and Het is a 5- or 6-membered heterocyclic aromatic ring, optionally benzocondensed, containing 1 to 3 heteroatoms selected from the group consisting of oxygen, nitrogen and sulphur, linked through a carbon atom or through a nitrogen atom;
 c) $C_3$-$C_7$ cycloalkyl optionally containing unsaturations; and
 d) 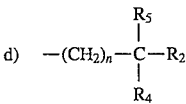

wherein
n is 0 or 1 to 4;
$R_2$ is hydrogen, methyl or phenyl;
$R_4$ is OH, $NH_2$ or dialkylamino;
$R_5$ is hydrogen, $C_1$-$C_6$ linear or branched alkyl, $C_5$-$C_6$ cycloalkyl; and $R_3$ is $C_1$-$C_6$ alkyl, $C_3$-$C_7$-cycloalkyl, phenyl or benzyl.

8. A pharmaceutical composition containing a compound of claim 1 in admixture with a suitable pharmaceutical carrier.

* * * * *